(12) United States Patent
Doric et al.

(10) Patent No.: US 10,274,712 B2
(45) Date of Patent: Apr. 30, 2019

(54) MICROSCOPE FOR FLUORESCENCE IMAGING WITH VARIABLE FOCUS

(71) Applicant: Optomak, Inc., Quebec (CA)

(72) Inventors: Sead Doric, L'Ancienne-Lorette (CA); Harold Dehez, Quebec (CA); Marie-Andrée Houle, Quebec (CA)

(73) Assignee: OPTOMAK, INC. (CA)

( * ) Notice: Subject to any disclaimer, the term of this patent is extended or adjusted under 35 U.S.C. 154(b) by 22 days.

(21) Appl. No.: 15/695,484

(22) Filed: Sep. 5, 2017

(65) Prior Publication Data
US 2017/0363849 A1 Dec. 21, 2017

Related U.S. Application Data

(63) Continuation-in-part of application No. 15/232,371, filed on Aug. 9, 2016, now Pat. No. 9,846,300, which
(Continued)

(51) Int. Cl.
*G02B 21/00* (2006.01)
*G02B 21/08* (2006.01)
(Continued)

(52) U.S. Cl.
CPC .......... *G02B 21/082* (2013.01); *A61B 5/0071* (2013.01); *A61B 5/0084* (2013.01);
(Continued)

(58) Field of Classification Search
CPC ...... G02B 21/00; G02B 21/082; G02B 13/14; G02B 13/0095; G02B 6/0006;
(Continued)

(56) References Cited

U.S. PATENT DOCUMENTS

| 6,101,028 A | 8/2000 | Heacock et al. |
| 6,508,759 B1 | 1/2003 | Taylor et al. |

(Continued)

FOREIGN PATENT DOCUMENTS

| WO | WO 2016187715 A1 | 12/2016 |
| WO | WO 2017079688 A1 | 5/2017 |

OTHER PUBLICATIONS

Adam M Packer, Botond Roska, & Michael Häusser, "Targeting neurons and photons for optogenetics", nature neuroscience, vol. 16, No. 7, July 2013, pp. 268-280. (Year: 2013).*

(Continued)

*Primary Examiner* — William R Alexander
(74) *Attorney, Agent, or Firm* — Mitch Harris, Atty at Law, LLC; Andrew M. Harris

(57) ABSTRACT

A miniaturized microscope having a tunable focal length provides for fluorescence measurements at an adjustable focus, providing for autofocus and/or depth adjustment of an image measurement without altering or adjusting a probe implanted in a sample and while providing collimated illumination of an area within the sample. The microscope includes an objective lens having a fixed position with respect to a second connector for receiving light returning from the sample and focusing it on an image sensor within the microscope that generates an image output, a beamsplitter for separating light returning from the sample, and an electrically-tunable lens positioned between the objective lens and the image sensor for adjusting an optical path length from the optical interface to the image sensor. The illumination is focused at or near a back focal plane of the objective lens to the sample, providing collimated or quasi-collimated illumination on or within the sample.

17 Claims, 12 Drawing Sheets

Related U.S. Application Data is a continuation-in-part of application No. 14/991,208, filed on Jan. 8, 2016, now Pat. No. 9,791,683.

(51) Int. Cl.

| | | |
|---|---|---|
| *G02B 13/00* | (2006.01) | |
| *G02B 21/02* | (2006.01) | |
| *F21V 8/00* | (2006.01) | |
| *G02B 27/14* | (2006.01) | |
| *G02B 21/16* | (2006.01) | |
| *A61N 5/06* | (2006.01) | |
| *A61B 5/00* | (2006.01) | |
| *G02B 13/14* | (2006.01) | |
| *G02B 21/18* | (2006.01) | |
| *G02B 21/36* | (2006.01) | |

(52) U.S. Cl.
CPC .......... *A61N 5/0622* (2013.01); *G02B 6/0006* (2013.01); *G02B 13/0095* (2013.01); *G02B 21/0008* (2013.01); *G02B 21/02* (2013.01); *G02B 21/16* (2013.01); *G02B 27/141* (2013.01); *G02B 13/14* (2013.01); *G02B 21/18* (2013.01); *G02B 21/361* (2013.01)

(58) Field of Classification Search
CPC ........ G02B 21/02; G02B 21/16; G02B 21/18; G02B 27/141; A61B 5/0071; A61B 5/0084; A61N 5/0622
USPC .......................................................... 359/363
See application file for complete search history.

(56) References Cited

U.S. PATENT DOCUMENTS

| | | | |
|---|---|---|---|
| 6,643,071 B2 | 11/2003 | Schnitzer | |
| 6,846,311 B2 | 1/2005 | Gatto | |
| 6,847,480 B2 | 1/2005 | Steenblik et al. | |
| 7,262,923 B2 | 8/2007 | Quake et al. | |
| 7,978,346 B1 * | 7/2011 | Riza .................. | G01B 11/24 356/368 |
| 8,346,346 B1 | 1/2013 | Schnitzer et al. | |
| 8,624,967 B2 | 1/2014 | O'Connell et al. | |
| 8,840,566 B2 | 9/2014 | Seibel et al. | |
| 9,046,659 B2 | 6/2015 | Doric | |
| 9,195,043 B2 | 11/2015 | Ghosh et al. | |
| 9,207,405 B2 | 12/2015 | Doric | |
| 9,409,036 B2 | 8/2016 | Klorg | |
| 9,476,832 B2 | 10/2016 | Walla et al. | |
| 9,696,897 B2 | 7/2017 | Garcia | |
| 2006/0187499 A1* | 8/2006 | Natori .................. | G02B 21/0032 358/474 |
| 2006/0250687 A1* | 11/2006 | Karaki ................ | G02B 21/0012 359/368 |
| 2008/0252966 A1* | 10/2008 | Karaki ................ | G02B 21/0004 359/391 |
| 2010/0007947 A1 | 1/2010 | Lembke | |
| 2010/0053539 A1* | 3/2010 | Lin .................... | G02F 1/13 349/200 |
| 2011/0224554 A1 | 9/2011 | Vukeljic et al. | |
| 2012/0140057 A1* | 6/2012 | Borck ................ | G01N 21/6458 348/79 |
| 2014/0036364 A1 | 2/2014 | Doric | |
| 2014/0049682 A1* | 2/2014 | Galstian .............. | G02B 7/38 348/356 |
| 2015/0309295 A1 | 10/2015 | Cocker et al. | |
| 2015/0366437 A1 | 12/2015 | Labrie et al. | |
| 2016/0131334 A1 | 5/2016 | Rousseau et al. | |
| 2017/0059841 A1 | 3/2017 | Trulson et al. | |
| 2017/0143934 A1* | 5/2017 | Tsai .................... | A61H 23/00 |
| 2017/0199364 A1 | 7/2017 | Doric et al. | |
| 2017/0199369 A1 | 7/2017 | Doric et al. | |
| 2018/0140172 A1* | 5/2018 | Hu .................... | A61B 1/042 |
| 2019/0053712 A1* | 2/2019 | Rogers .............. | A61B 5/0084 |

OTHER PUBLICATIONS

Ramin Pashaie and Ryan Falk, "Single Optical Fiber Probe for Fluorescence Detection and Optogenetic Stimulation", IEEE Transactions on Biomedical Engineering, vol. 60, No. 2, Feb. 2013, pp. 805-815. (Year: 2013).*

Ghosh, et al., "Miniaturized integration of a fluorescence microscope", Nature Methods, Oct. 2011, pp. 871-882, vol. 8, No. 10, Nature Publishing Group, London.

Ziv, et al., "Long-term dynamics of CA1 hippocampal place codes", Nature Neuroscience, Feb. 2013, 5 pages (pp. 1-5 in pdf), 16(3).

Flusberg, et al., "High-speed, miniaturized fluorescence microscopy in freely moving mice", Nature Methods, Nov. 2008, pp. 935-938, vol. 5, No. 11, Nature Publishing Group, London.

Helmchen, et al., "A Miniature Head-Mounted Two-Photon Microscope: High-Resolution Brain Imaging in Freely Moving Animals", Neuron, Sep. 27, 2001, pp. 903-912, vol. 31, Cell Press.

Murakami, et al., "A Miniature Confocal Optical Microscope with MEMS Gimbal Scanner", 12th International Conference on Solid-State Sensors, Actuators and Microsystems, Jun. 8-12, 2003, pp. 587-590, Boston, US.

Bergeron, "Fingertip-size microscope has huge potential for studying the brain and its diseases, say Stanford researchers", Sep. 16, 2011, downloaded from http://news.stanford.edu/news/2011/september/fingertip-size-microscope-091611.html on Apr. 30, 2017, 6 pages (pp. 1-6 in pdf).

Baker, Abbas El Gamal and Mark Schnitzer: "Two-gram microscopes make brain images in moving mice", Nature Methods, Oct. 2011, pp. 781, vol. 8, No. 10, Nature America, Inc.

U.S. Appl. No. 62/383,122, filed Sep. 2, 2016, 132 pages (pp. 1-132 in pdf).

U.S. Appl. No. 62/251,501, filed Nov. 5, 2015, 70 pages (pp. 1-70 in pdf).

Notice of Allowance in U.S. Appl. No. 14/991,208, dated Jun. 2, 2017, 9 pages (pp. 1-9 in pdf).

Office Action in U.S. Appl. No. 14/991,208 dated May 4, 2017, 10 pages (pp. 1-10 in pdf).

Notice of Allowance in U.S. Appl. No. 14/991,208 dated Jul. 26, 2017, 10 pages (pp. 1-10 in pdf).

* cited by examiner

MICROSCOPE FOR FLUORESCENCE IMAGING WITH VARIABLE FOCUS

This U.S. Patent Application is a Continuation-in-Part of U.S. patent application Ser. No. 15/232,371 filed on Aug. 9, 2016 and published as U.S. Patent Application Publication No. 20170199369 on Jul. 13, 2017, which is a Continuation-in-Part of U.S. patent application Ser. No. 14/991,208, filed on Jan. 8, 2016 and published as U.S. Patent Application Publication No. 20170199364 on Jul. 13, 2017, and claims priority thereto under 35 U.S.C. § 120. The disclosure of the above-referenced U.S Patent Application is incorporated herein by reference.

BACKGROUND OF THE INVENTION

1. Field of the Invention

The present invention relates to biological microscopy, and more particularly concerns a microscope probe for in vivo or in vitro fluorescence imaging with a variable focal position.

2. Background of the Invention

When making microscopic observations of in vivo biological specimens, minimally invasive techniques are required. However, conventional microscopes feature large size microscope objectives. Large objectives cannot be implanted within a sample without causing significant damage to the sample, such as removing structures in order to facilitate access to deep layers within the sample. Less invasive Gradient Index relay (GRIN)-optic cannula-based microscopes may be used in optogenetics experiments, such as those disclosed in U.S. Patent Application Publication Nos. US20170199364A1 and US20170199369A1, but have a fixed working distance, i.e., the probes have a fixed object plane and focus. Such probes require placement of the end of a fiber optic or other probe in proximity to the observation location of the image and can only observe fluorescent emissions or structures at the fixed observation location.

Therefore, it would be desirable to provide an optogenetic compatible microscope having a compact size and capable of observing images at multiple object planes/focal lengths.

SUMMARY OF THE INVENTION

The invention encompasses microscopes capable of performing optogenetic stimulation and fluorescence, and/or other imaging on a sample at an adjustable object plane.

The microscope includes a microscope body with a first connector that receives light from an illumination source and a second connector that connects to a cannula and optically aligns the cannula with the microscope body. The second connector has an optical interface for coupling light returning from the sample to the microscope and illumination from the illumination source to the sample. The microscope also includes an objective lens having a fixed position with respect to the second connector for receiving the light returning from the sample, an image sensor for generating an image from the light returning from the sample, a beamsplitter positioned between the objective lens and the image sensor for separating the light returning from the sample from the illumination, and an electrically-tunable lens positioned between the objective lens and the image sensor for adjusting an optical path length between the at least one optical interface and the image sensor. By adjusting a voltage supplied to the electrically-tunable lens, a focus of the image or a depth of the image within the sample is adjusted. The illumination provided from the illumination source to the sample is focused at or near to the back focal plane of the objective lens, so that the objective lens collimates or quasi-collimates the illumination provided to the sample, while the objective lens focuses light returning from the sample on the image sensor(s).

The microscope can be implemented as a dual-wavelength system in which multiple image sensors are used to provide multiple images at different wavelengths, and filters are incorporated in the optical paths between the objective lens and the image sensors.

The foregoing and other objectives, features, and advantages of the invention will be apparent from the following, more particular, description of the preferred embodiment of the invention, as illustrated in the accompanying drawings.

BRIEF DESCRIPTION OF THE DRAWINGS

The novel features believed characteristic of the invention are set forth in the appended claims. The invention itself, however, as well as a preferred mode of use, further objectives, and advantages thereof, will best be understood by reference to the following detailed description of an illustrative embodiment when read in conjunction with the accompanying drawings, wherein like reference numerals indicate like components, and:

DESCRIPTION OF ILLUSTRATED EMBODIMENT

Figure 1:
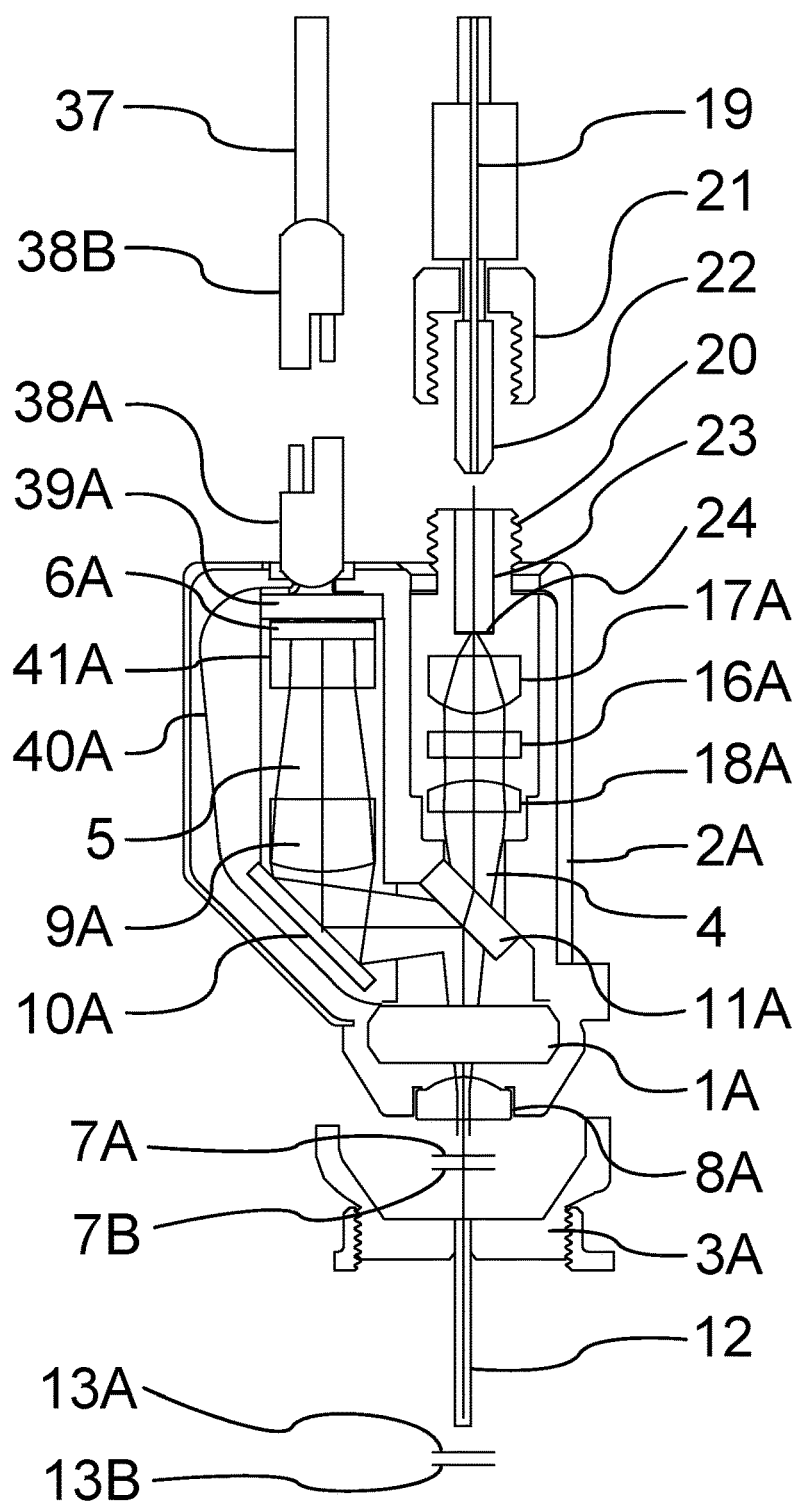
FIG. 1 is a side cross-section view and FIG. 2 is a front cross-section view of an exemplary miniaturized multimodal microscope system.

The systems described herein are miniaturized microscopes systems of generally less than a cubic inch in size that provide for focal path length adjustment for focusing and/or imaging depth adjustment via an electrically-tunable lens and one or more internal image sensors. Typical mechanically adjustable microscopes are bulky and are traditionally limited to tabletop applications. Adjusting the length of the optical path between the imaged region on or in the sample and the image sensor(s) can be changed by up to 500 µm by adjusting a voltage supplied to the electrically-tunable lens, which can accommodate changes in the position of a region of interest on or in the sample. The electrically-tunable microscope systems provided in the following examples have increased repeatability in focus, reduces the overall size of the microscope and provides more robust operation. An application for the microscopes disclosed herein is fluorescence imaging of fluorescent proteins for applications requiring monitoring of cell activity. The system includes an objective lens to create a magnified image of a region of the sample on the image sensor integrated within the microscope. The objective lens may be integrated in the microscope or be integrated in a cannula to which the microscope is attached. The microscope includes an optical splitter to separate illumination light from fluorescence signals. The illumination is focused at or near the back focal plane of the objective lens, so that the illumination is collimated or quasi-collimated at the imaging plane(s) at or within the sample.

In one implementation of the microscope, two or more illumination wavelengths are provided to the microscope for illuminating the sample, e.g., stimulating fluorescent emissions from the sample, and the microscope also includes a second image sensor and another optical splitter to separate the light returning from the sample into two images for measurement by the image sensors. In some applications of the multi-wavelength implementation of the microscope, a sample may be labeled with two different fluorescent markers having distinct fluorescence emission spectra and distinct excitation spectra, which avoids cross-talk between measurement channels. While the first marker is used to measure activity, the second marker may be present as a reference, or also for cell activity monitoring. Providing two different fluorescence measurement channels provides for simultaneous capture of images due to the presence of the two fluorescent markers.

The miniaturized microscope disclosed herein is configured to easily connect to and disconnect from the cannula and includes a specific connector adapted to provide precise optical alignment with the cannula, which may be a cannula such as those described in U.S. Pat. No. 9,195,043 and U.S. Patent Application Publication U.S. 20150309295A1, the disclosures of which are incorporated herein by reference. The imaging system is designed to observe one or many fields of view smaller than 0.5 mm$^2$ (to reduce invasiveness) with a spatial resolution at the micron scale. An optical splitter set is included to separate one or more bands of illumination light from the fluorescence signal returning from the sample, to provide the illumination light to the sample, and to separate the fluorescence signals and direct them to corresponding image sensors. The objective lens may be incorporated in the microscope body, or in the cannula and may image light from an implant inserted in the sample, which may be a relay lens, e.g. a GRIN lens, and/or a glass rod. Alternatively, the objective lens may image one or more regions near the surface of the sample or at some depth within a transparent or translucent sample. Other configurations and combinations, such as those disclosed herein or otherwise provided by combining elements that are shown by the present disclosure or their equivalents, are contemplated and the examples chosen as illustrations should not be considered limiting. In the examples given herein, the field of view of the microscope described herein is less than 0.5 mm$^2$ and having a spatial resolution at the micron scale, which also differs from existing miniature microscope systems. By limiting the field of view to less than 0.5 mm$^2$, the volume of the microscope can be reduced and the image quality improved over the field of view. To improve the portability and facilitate the access to a confined region of interest, the total size of the miniaturized microscope can be maintained below 3 cm$^3$ with a weight of under 8 g.

Figure 2:
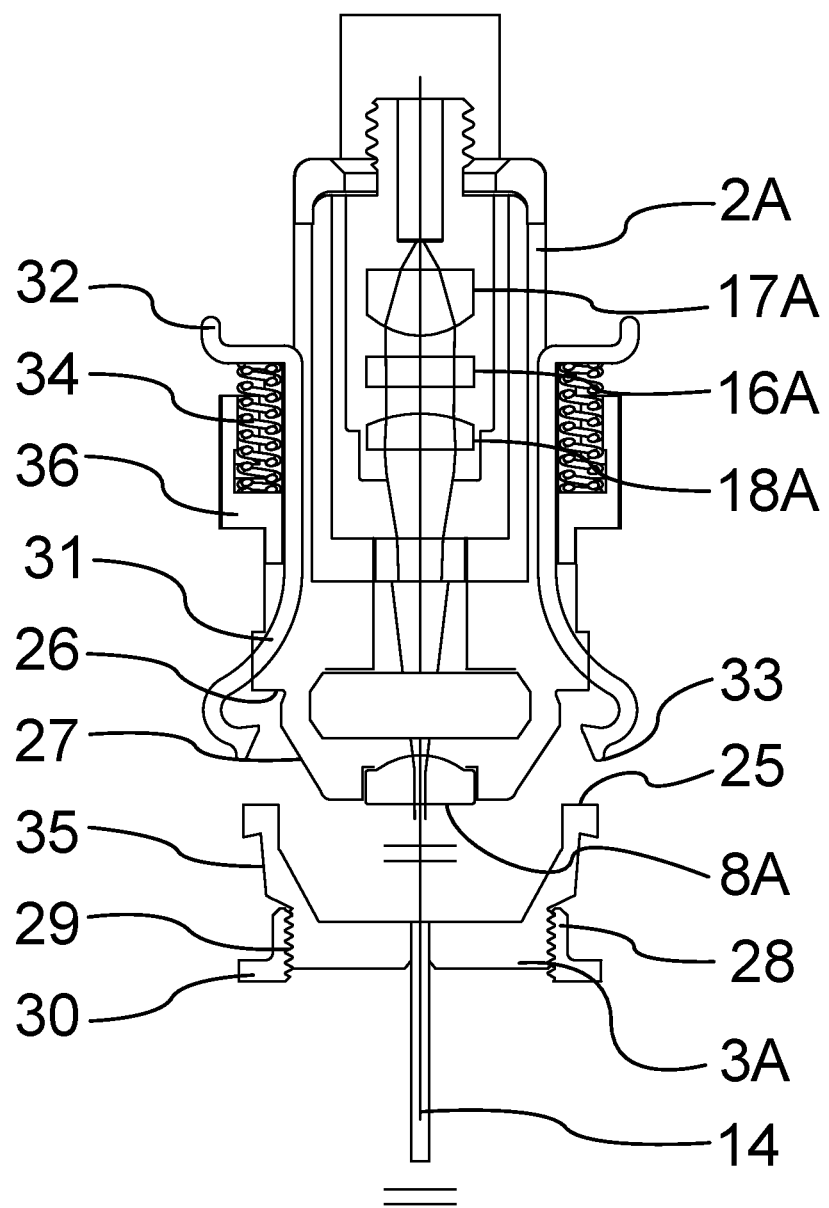

Referring now to FIG. 1 and FIG. 2, an example of a miniaturized microscope system for fluorescence measurement is shown in a side cross-section view and front cross-section view, respectively. A microscope body 2A has a connector adapted for connection to a cannula 3A that is attached to a sample, which is generally a biological test specimen for in vivo measurements as described in the above-incorporated U.S. Patent and U.S. Patent Application Publication, and the latching and keying mechanisms may be employed in the example microscopes described herein. The microscope, which includes microscope body 2A, also includes an optical interface below a lower surface of an objective lens 8A at an object plane 7A or 7B of the optical system, and a dichroic filter (e.g., a dichroic mirror) 11A to separate the returning image from the sample from the illumination pathway so that returning light from the sample is directed toward an image sensor 6A, such as a CMOS sensor array. The returning light is magnified by less than 10× between the object plane 7A or 7B below the lower surface of objective lens 8A and image sensor 6A. Image sensor 6A is connected to an external imaging system via a connector 38A that receives a plug 38B which detachably connects to a cable 37 provided from the imaging system. The magnification is provided by objective lens 8A and a tube lens 9A in combination. To optimize aberration correction and increase the numerical aperture of the microscope, the exemplary microscope system features a high power aspheric lens as objective lens 8A, which in the example has a numerical aperture between 0.3 and 0.6. To reduce the total size of the system, the focal length of the objective lens 8A, the length of a detection optical pathway 5, and the focal length of tube lens 9A are chosen to produce a magnification ratio between 2× and 10× between object planes 7A,7B and image sensor 6A. The insertion of tube lens 9A in detection optical pathway 5 also reduces the angular divergence at the surface of dichroic filter 11A and therefore improves the efficiency of dichroic filter 11A. For compactness, a folding mirror 10A, which may be metallic or dielectric, is included in detection optical pathway 5.

Adjustment of the optical path length of detection optical pathway 5 is provided by a low-optical-power electrically-tunable lens 1A, which may be positioned before dichroic filter 11A, but after objective lens 8A, as shown, or alternatively positioned after dichroic filter 11A along detection optical pathway 5. Use of a low-optical-power objective lens allows the illumination to remain collimated or quasi-collimated at a position of the imaging plane, i.e., the object plane of the system. The optical power of the electrically tunable lens can be electrically adjusted between −20 and +20 diopters. A voltage provided to electrically-tunable lens 1A via an electrical cable 40A, which may be a flexible circuit strip or wires connected from a circuit board 39A and thereby from connector 38A, is varied to adjust the position of object planes 7A, 7B of the microscope system to any position between a proximal position at object plane 7A and a distal position at object plane 7B. The components of the three-lens system included in detection optical pathway 5, i.e., objective lens 8A, electrically-tunable lens 1A and tube lens 9A are selected to minimize variation in the magnification when adjusting the working distance of the microscope system. Electrically-tunable lens 1A can be of a type in which the mechanical thickness and/or shape of at least a portion of electrically-tunable lens 1A is adjusted via applied voltage and current. The applied voltage and current adjusts the curvature and/or the position of one or both external faces of electrically-tunable lens 1A and/or the curvature and/or position of one or more internal interfaces of electrically-tunable lens 1A, to alter the focal length of electrically-tunable lens 1A. Examples of such electrically-tunable lens 1A are, e.g., an electro-wetted lens, a shape-changing polymer lens, a liquid lens, etc. Alternatively, or in combination, electrically-tunable lens 1A may be a lens in which the refractive index of a media is adjusted to adjust the optical path length, e.g., a liquid crystal lens.

In the illustrated example, a gradient index (GRIN) relay lens 12 extends into the sample to image a region of interest and to optically excite fluorescent molecules and/or optically stimulate light-activated ion channels present in the sample in the region of interest. GRIN relay lens 12 is used to relay an image from an object plane within the range of an object plane 13A to an object plane 13B imaging deep structures in the sample to the corresponding object planes 7A to 7B at cannula 3A. Changing the position of the object plane of the microscope by varying the voltage supplied to electrically-tunable lens 1A to select an object plane lying between or at one of object planes 7A,7B, will cause the microscope system to image at a depth between corresponding object planes 13A, 13B, providing a working distance that varies between the distance from the distal tip of GRIN relay lens 12 to object plane 13A and the distance from the distal tip of GRIN relay lens 12 to object plane 13B. GRIN relay lens 12 is integrated in cannula 3A and is optically aligned with an optical axis 14 of objective lens 8A. GRIN relay lens 12 is not required for imaging surfaces just below objective lens 8A.

An illumination optical pathway 4 extends from a second threaded male connector 20. A bored recess 23 at the top of microscope body 2A receives an optical coupling, such as from a tip 22 of an optical fiber 19 to a hub 24 provided below second threaded male connector 20, from at least one illumination source that provides light for exciting fluorescence in the sample, and optionally another illumination source for providing optogenetic stimulation. A threaded female connector 21 detachably couples optical fiber 19 to microscope body 2A by twisting threaded female connector 21 onto threads of second threaded male connector 20. To avoid imaging artifacts due to illumination discontinuities, the illumination optical pathway 4 is configured to provide uniform illumination over the total field of view between object planes 7A and 7B. Illumination optical pathway 4 is configured so that the output of optical fiber 19 is imaged at, or close to, the back focal plane of objective lens 8A, ensuring that dust or defects that may accumulate at the bottom of hub 24 after optical fiber 19 has been repeatedly connected and disconnected are not imaged in the object plane of the microscope system. When the output of optical fiber 19 is imaged at the back focal plane of objective lens 8A or close to the back focal plane of objective lens 8A, the illumination light is collimated or quasi-collimated on the sample. In the illustrated example, an illumination lens system along illumination pathway 4 includes a high numerical aperture aspheric lens 17A that forms a beam collimated on an excitation filter 16A, reducing the angle of incidence of light at the surface of excitation filter 16A, improving filtering efficiency. The collimated beam filtered by excitation filter 16A is then focused on the back focal plane of objective lens 8A by a plano-convex lens 18A. As mentioned above, in the depicted embodiment, electrically-tunable lens 1A is located between dichroic filter 11A and objective lens 8A, so that electrically-tunable lens 1A lies within illumination optical pathway 4 as well as detection optical pathway 5. Since the illumination light is collimated or quasi-collimated on the sample, i.e., at the particular object plane being imaged (either between object planes 13A and 13B if GRIN relay lens 12 is included, or between object planes 7A and 7B if GRIN relay lens 12 is not included), the variation in focal length of low-optical-power electrically-tunable lens 1A has minimal effect on the illumination provided at the sample. In other embodiments, the illumination field and the field of view of the illumination and illumination optical pathway 4 may change. Excitation filter 16A includes at least one optical transmission band corresponding to the nominal wavelength of the illumination source(s) coupled through second threaded male connector 20, and cleans the illumination light before it is introduced to GRIN relay lens 12, removing light artifacts such as auto-fluorescence generation in the optical fiber 19 coupling the illumination light to second threaded male connector 20. An emission filter that has a transmission band that admits light at the expected fluorescence wavelength of the sample may be included in detection optical pathway 5, e.g., by a dichroic coating on folding mirror 10A, preventing light from the illumination source(s) entering image sensor 6A and/or with an additional emission filter 41A in pathway 5.

FIG. 2 additionally shows further details of an attachment mechanism for cannula 3A, a cannula similar to which is described in detail in the above-incorporated references. In the depicted embodiment, use of such a cannula provides convenient attachment and removal of microscope body 2A from cannula 3A, but is not a requirement to practice the invention, except as recited in particular Claims. The interior of cannula 3A is shaped to adapt cannula 3A to accept a guiding taper 27 around the bottom portion of microscope body 2A and a cylindrical shoulder 25 contacts a corresponding shoulder 26 on microscope body 2A to prevent movement of microscope body 2A with respect to cannula 3A once microscope body 2A is secured to cannula 3A. Shoulder 25 defines a slot 35 around the exterior surface of cannula 3A. A precise optical alignment between objective lens 8A and GRIN relay lens 12 is achieved once microscope body 2A is secured to cannula 3A. As seen in FIG. 2, additional components that secure microscope body 2A to cannula 3A are shown. Latch hooks 33 at the end of a pair of latches 31 capture slot 35 to hold shoulder 25 when latches 31 are expanded as inner surfaces of latches 31 slide along microscope body 2A. Microscope body 2A is shaped to form an acute angle with respect to the cylindrical axis of cannula 3A, so that, when latches 31 are moved downwards toward cannula 3A, microscope body 2A acts as a guide for expanding latch hooks 33 to release shoulder 25 of cannula 3A. The upper end of latches 31 forms a retention shoulder 32 which compresses a compression spring 34 that provides for secure latching of latch hooks 33 by pressing against the lower surface of retention shoulder 32 and a shoulder 36 of microscope body 2A to pull latches 31 upwards. Cannula 3A and microscope body 2A are connected by compressing spring 34 and pressing on latches 31 toward cannula 3A. In other embodiments, horizontal springs can be added in microscope body 2A to press on latch to press on latches 31 toward cannula 3A and secure latch hook 33 in slot 35. A pin may be inserted between latch hooks 33 and cannula 3A to release latch hooks 33 from slot 35. Cannula 3A is secured to the specimen being observed, in general, by fastening a flange 30 of an adjustment ring 28 of cannula 3A to the specimen with an adhesive and/or with fasteners such as screws. Flange 30 is attached to a body 29 of cannula 3A. To adjust the coarse focus and working distance of the microscope system (or to adjust the penetration depth of GRIN relay lens 12 if present), adjustment ring 28 can be rotated to alter the distance between flange 30 and objective lens 8A. In the example, body 29 of cannula 3A includes a male threaded portion on an outer surface. A threaded female inner surface of adjustment ring 28 mates with a threaded male portion of body 29 and is rotated to adjust the distance between the microscope system and the specimen (or the penetration depth of GRIN relay lens 12) when adjustment ring 28 is attached to the specimen.

Figure 3:
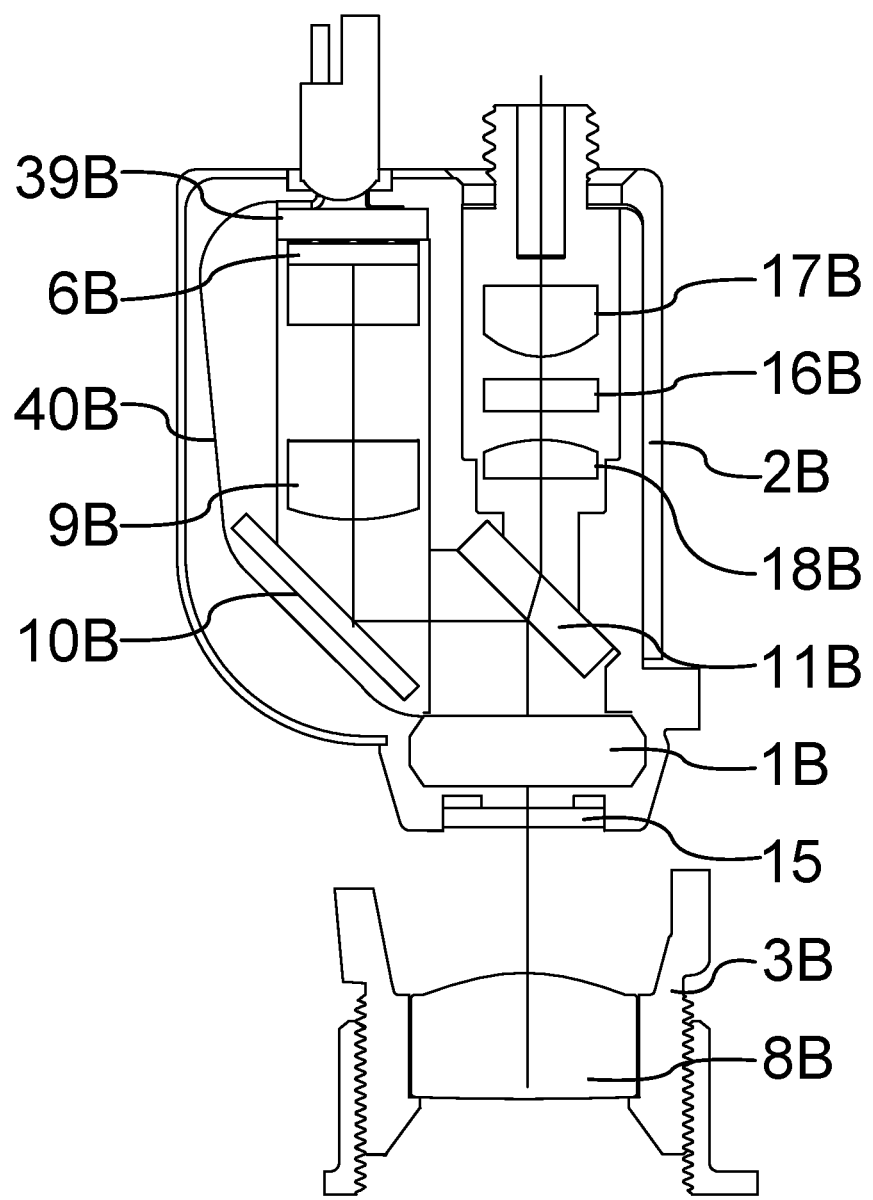
FIG. 3 is a side cross-section view of another exemplary miniaturized multimodal microscope system.

Referring now to FIG. 3, another example of a microscope system for fluorescence measurement and/or optogenetic stimulation is shown in a side cross-section view. The microscope system of FIG. 3 differs from the microscope system of FIGS. 1-2 in that an objective lens 8B is integrated in a cannula 3B. Since the optical paths differ from the microscope system of FIGS. 1-2, a high numerical aperture aspheric lens 17B, a plano-convex spherical lens 18B, an excitation filter 16B, a folding mirror 10B, a tube lens 9B and an image sensor 6B may be of different dimensions than their counterparts in FIG. 1. A dichroic filter 11B, an electrically-tunable lens 1B and a microscope body 2B also generally have differing dimensions from their counterparts in the microscope system of FIGS. 1-2, however the remainder of the components integrated within microscope body 2B are similar or identical to and perform the same functions as the components in the microscope system of FIGS. 1-2, including the connection of electrically-tunable lens 1B to a circuit board 39B via a cable 40B. By including a high numerical aperture objective lens 8B in cannula 3B, the working distance is increased up to 2.5 mm and the image field of view is increased up to 0.5 mm$^2$ without increasing invasiveness in the subject and no GRIN relay lens is required in the sample. An output window 15 is included at the bottom of microscope body 2B to seal the microscope.

Figure 4:
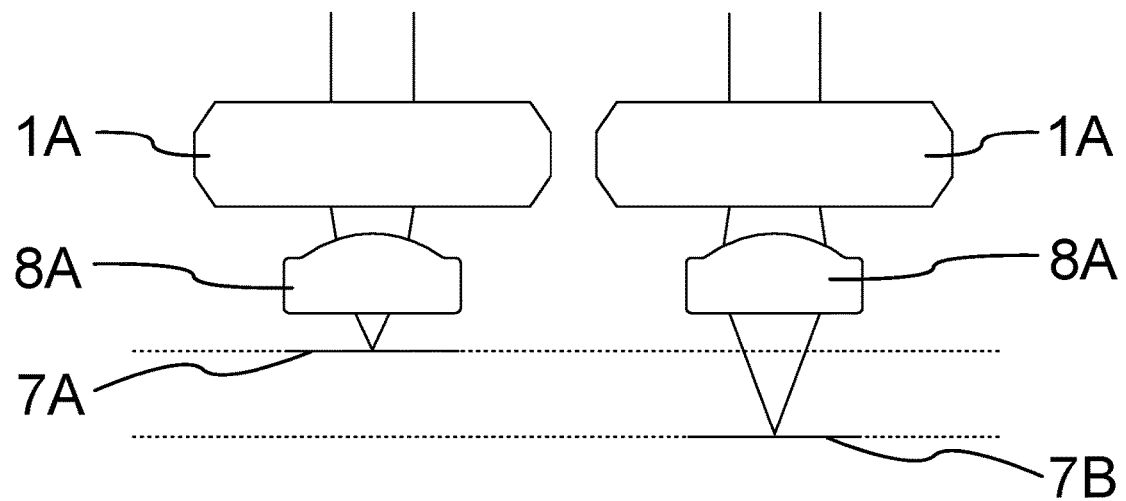
FIG. 4 is a pictorial view showing movement of the imaging plane in the microscope systems of FIGS. 1-2 and FIG. 3.

Referring now to FIG. 4, a pictorial view illustrates operation of the microscope of FIGS. 1-2 and the microscope of FIG. 3 without GRIN relay lens 12. In the left side of FIG. 4, electrically-tunable lens 1A is supplied a voltage so that object plane 7A is focused on image sensor 6A in detection optical pathway 5 of FIG. 1. In the right side of FIG. 4, electrically-tunable lens 1A is supplied a different voltage so that object plane 7B is focused on image sensor 6A in detection optical pathway 5 of FIG. 1. By changing the voltage applied to electrically-tunable lens 1A any object plane between object plane 7A and object plane 7B can be selected for detection by image sensor 6A (or image sensor 6B in the microscope system of FIG. 3).

Figure 5:
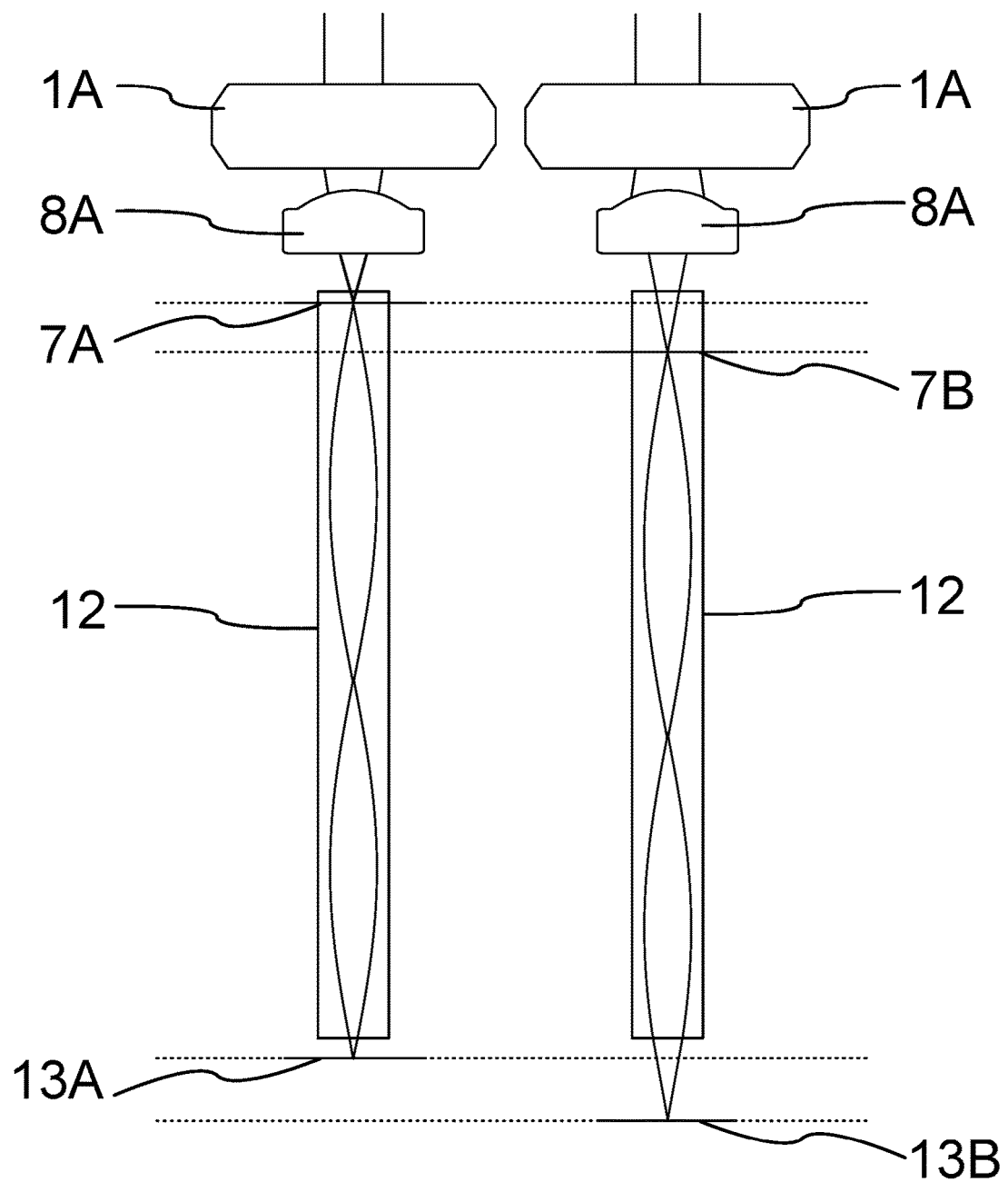
FIG. 5 is a pictorial view showing movement of the imaging plane in the microscope systems of FIGS. 1-2 and FIG. 3 when a relay lens is employed.

Referring now to FIG. 5, a pictorial view illustrates operation of the microscope of FIGS. 1-2 including GRIN relay lens 12. In the left side of FIG. 5, electrically-tunable lens 1A is supplied a voltage so that object plane 7A is focused on image sensor 6A in detection optical pathway 5 of FIG. 1, which refers object plane 13A through GRIN relay lens 12. In the right side of FIG. 5, electrically-tunable lens 1A is supplied a different voltage so that object plane 7B is focused on image sensor 6A in detection optical pathway 5 of FIG. 1, which refers object plane 13B through GRIN relay lens 12. By changing the voltage applied to electrically-tunable lens 1A any object plane between object plane 13A and object plane 13B can be selected for detection by image sensor 6A (or image sensor 6B in the microscope system of FIG. 3).

Figure 6:
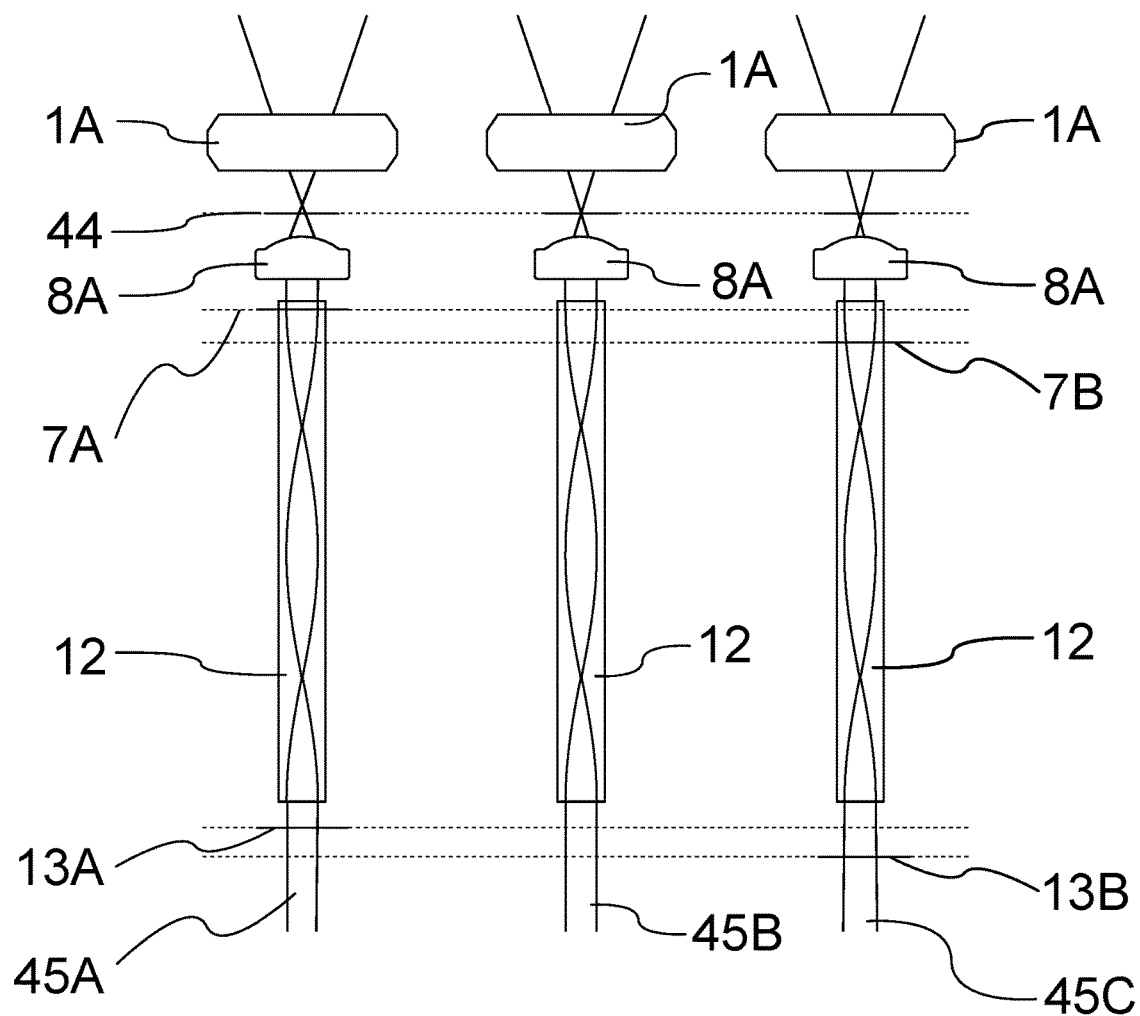
FIG. 6 is a pictorial view showing illumination handling in the microscope systems of FIGS. 1-2 and FIG. 3.

Referring now to FIG. 6, a pictorial view illustrates illumination handling by the microscope of FIGS. 1-2 and the microscope of FIG. 3. Illumination beams 45A-45C are collimated or quasi-collimated at the range of object planes 13A through 13B. Similarly, the illumination is substantially collimated at object planes 7A and 7B. To accomplish the collimation of the illumination, a focus of the illumination is located near to or at a back focal plane 44 of objective lens 8A, which collimates the illumination directed at the sample. The voltage applied to electrically-tunable lens 1A is varied to move the object plane of the microscope to any object plane 13A through object plane 13B (or object planes 7A-7B), but illumination beams 45A-45C are collimated or quasi-collimated throughout the range of object planes. As shown in FIG. 6, for a microscope optimized over the range of object planes 13A through 13B (or object planes 7A-7B), the illumination can be controlled to exactly collimate illumination beam 45B at the object plane for an image focus between object planes 13A through 13B (or object planes 7A-7B). Illumination beam 45A is then slightly convergent when the microscopy system is imaging at object plane 13A and illumination beam 45C is slightly divergent when the microscope system is imaging at object plane 13B.

Figure 7:
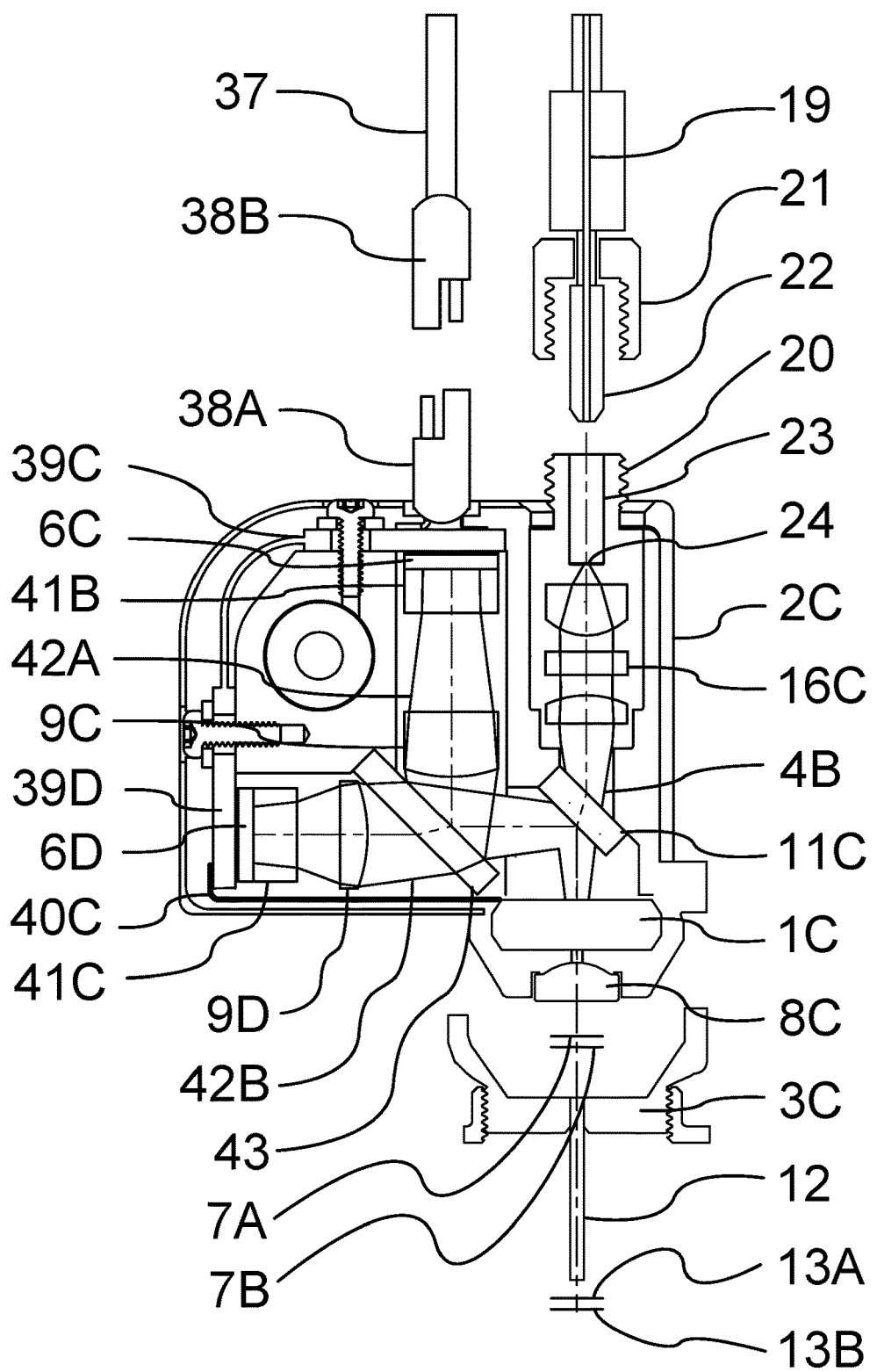
FIG. 7 is a side cross-section view of still another exemplary miniaturized multimodal microscope system.

Referring now to FIG. 7, yet another example of a microscope system for two-color fluorescence measurement is shown in a side cross-section view. The microscope system of FIG. 7 is similar to the microscope system of FIGS. 1-2 and FIG. 3, so only differences between them will be described in detail below. The microscope system of FIG. 7 includes multiple detection pathways and an illumination pathway 4B that receives light from at least two illumination sources coupled to optical fiber 19, with all of the illumination/stimulation light and received light passing through an objective lens 8C. Within a microscope body 2C, image sensors 6C and 6D are mounted on circuit boards 39C and 39D, respectively, and provide for simultaneous detection of a fluorescence image at two different wavelengths, provided through tube lenses 9C and 9D, respectively. A cannula 3C attaches to microscope body 2C and provides illumination to GRIN relay lens 12, as well as receiving light returning from the sample at two different wavelengths. The object plane of the system is again varied between object planes 13A, 13B (or object planes 7A, 7B if GRIN relay lens 12 is not employed) by varying a voltage supplied to an electrically-tunable lens 1C via an electrical cable 40C. A dichroic filter 43 replaces the function of folding mirrors 10A, 10B in FIGS. 1-3, and separates the first and second fluorescence images returning from the sample into light of a first wavelength or range directed along a first detection optical path 42A and light of a second wavelength or range directed along a second detection optical path 42B. Dichroic filter 43 passes the fluorescence image along a detection optical path 42B to image sensor 6D, and the second fluorescence image along a detection optical path 42A to image sensor 6C. A pair of image filters 41B and 41C are included in detection optical paths 42A, 42B, respectively to filter out any illumination that is reflected by a dichroic filter 11C, and to separate the two fluorescence images. While the illustrated example includes GRIN relay lens 12, the two-wavelength imaging system illustrated in FIG. 7 can be adapted for use without GRIN relay lens 12 and with objective lens 8C integrated in either microscope body 2C or cannula 3C, similar to the embodiment depicted in FIG. 3, as described above.

As mentioned above, electrical cable 37 provides the electrical interface to image sensors 6A-6D in the above-described microscope systems, as well as providing drive voltage to electrically-tunable lenses 1A-1C. Cable 37 includes the control and data signals needed to read image data from image sensors 6A-6D, as well as power to operate image sensors 6A-6D. While the illustrated system includes wired connections to image sensors 6A-6D and electrically-tunable lenses 1A-1C, in other examples the microscope system may be operated via wireless control using an integrated microcontroller and radio-frequency (RF) transceivers or optical transceivers. Further, the connections to the microscope systems may be made with rotary joints to prevent entanglement and alleviate stress that might otherwise be applied to the interface cables and fiber optics when used on freely moving specimens. A hybrid rotary joint incorporating electrical and fiber optic connections can be provided for this purpose.

Figure 8:
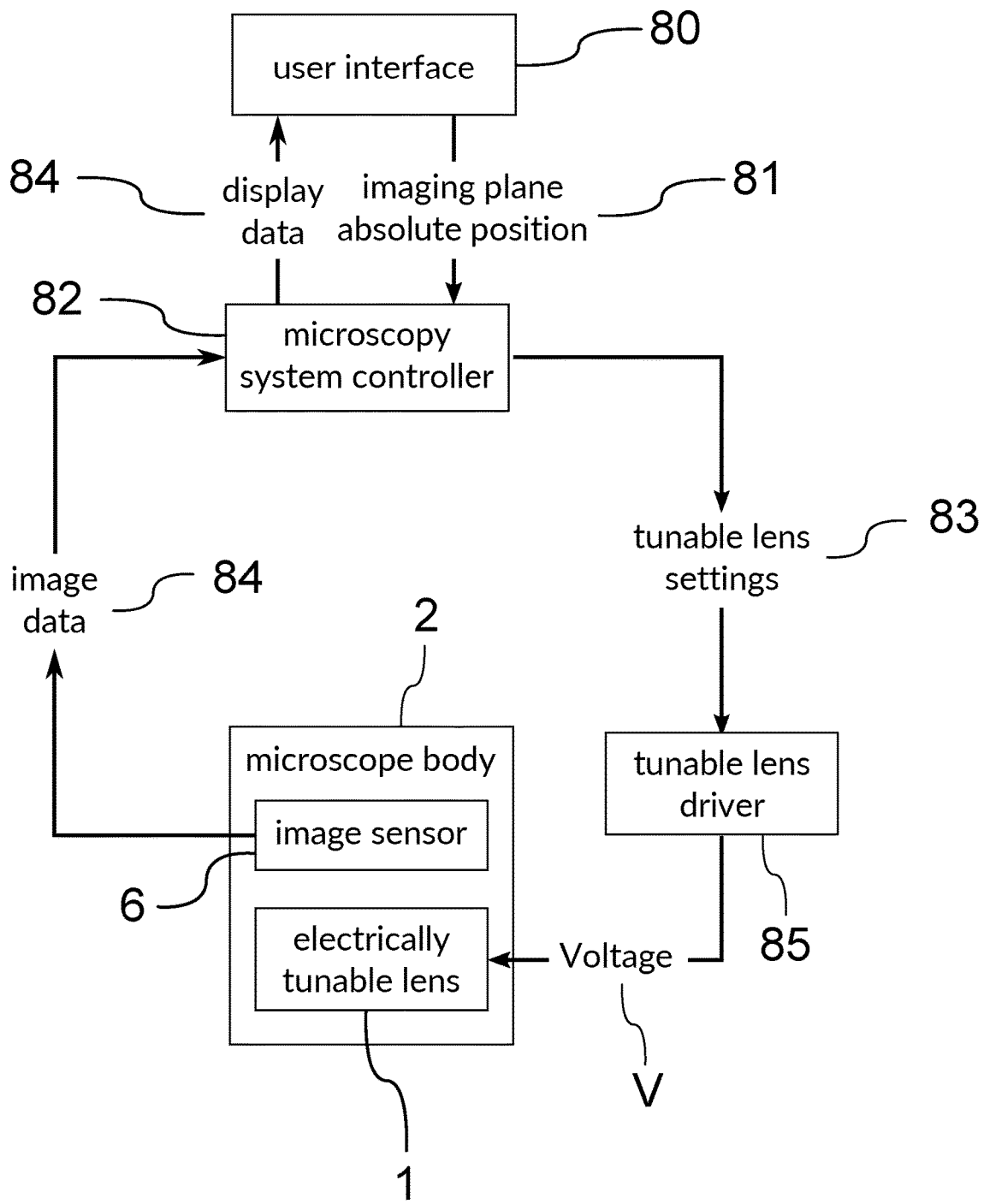
FIG. 8 is a block diagram of a microscope system with focal length adjustment for image depth change.

Referring now to FIG. 8, an imaging system in accordance with the examples given herein is shown in a functional block diagram. A microscope body 2 includes an image sensor 6 and an electrically-tunable lens 1. The output of image sensor 6 is provided to a microscopy system controller 82 that stores the collected (image) display data 84. Microscopy system controller 82 may be a general or special-purpose computer system. Microscopy system controller 82 sends a setting value 83 for controlling electrically-tunable lens 1 to a tunable lens driver 85, which, in response, generates an output voltage V that controls the focal length of electrically-tunable lens 1. Tunable lens driver 85 may be integrated into microscopy system controller 82, integrated in microscope body 2 or in the path of an electrical cable that interconnects microscopy body 2 with microscopy system controller 82. A user interface 80 receives input for controlling the operation of the imaging system of FIG. 8, and in particular, collects a user input 81 that directs the setting of the object plane depth of the microscope to microscopy system controller 82 to direct tunable lens driver 85 to adjust output voltage V supplied to electrically-tunable lens 1. While the above examples disclose providing an output voltage V it is understood that current may be controlled instead, depending on the requirements of the particular electrically-tunable lens 1 used in the system and generally a voltage and current are both supplied via the terminals that couple output voltage V to electrically-tunable lens 1.

During long term experiments, structures of interest within the sample may change depth. The above-described microscopes enable adjustment of the depth of the imaging plane between experiments to ensure that the same structures are imaged from one experiment to the next. Another important feature implemented in the systems disclosed herein is referencing an absolute depth of the imaging planes (e.g., object planes 7A and 7B in FIG. 1) beneath the objective lens (e.g., objective lens 8A of FIG. 1), and also referencing the absolute depth of the imaging planes (e.g., object planes 13A-13B of FIG. 1) below the GRIN lens 12, if GRIN lens 12 is present. Also, the mechanical interface between the microscope body 2A and cannula 3A is designed for optical connection repeatability, so that over repeated connections, the distance between imaging plane and the objective lens is identical for a given electrically-tunable lens control voltage V, and also identical for the distance between the imaging plane and the GRIN lens 12 for a control voltage V. Knowing the above-described distances and the relationship between the imaging plane shift and a change in control voltage V, the user can set an absolute working distance between the object plan (e.g., object planes 13A-13B of FIG. 1) and the GRIN lens 12, and the corresponding voltage V is sent to the tunable lens by tunable lens driver 85 under the control of microscopy system controller 82.

Figure 9:
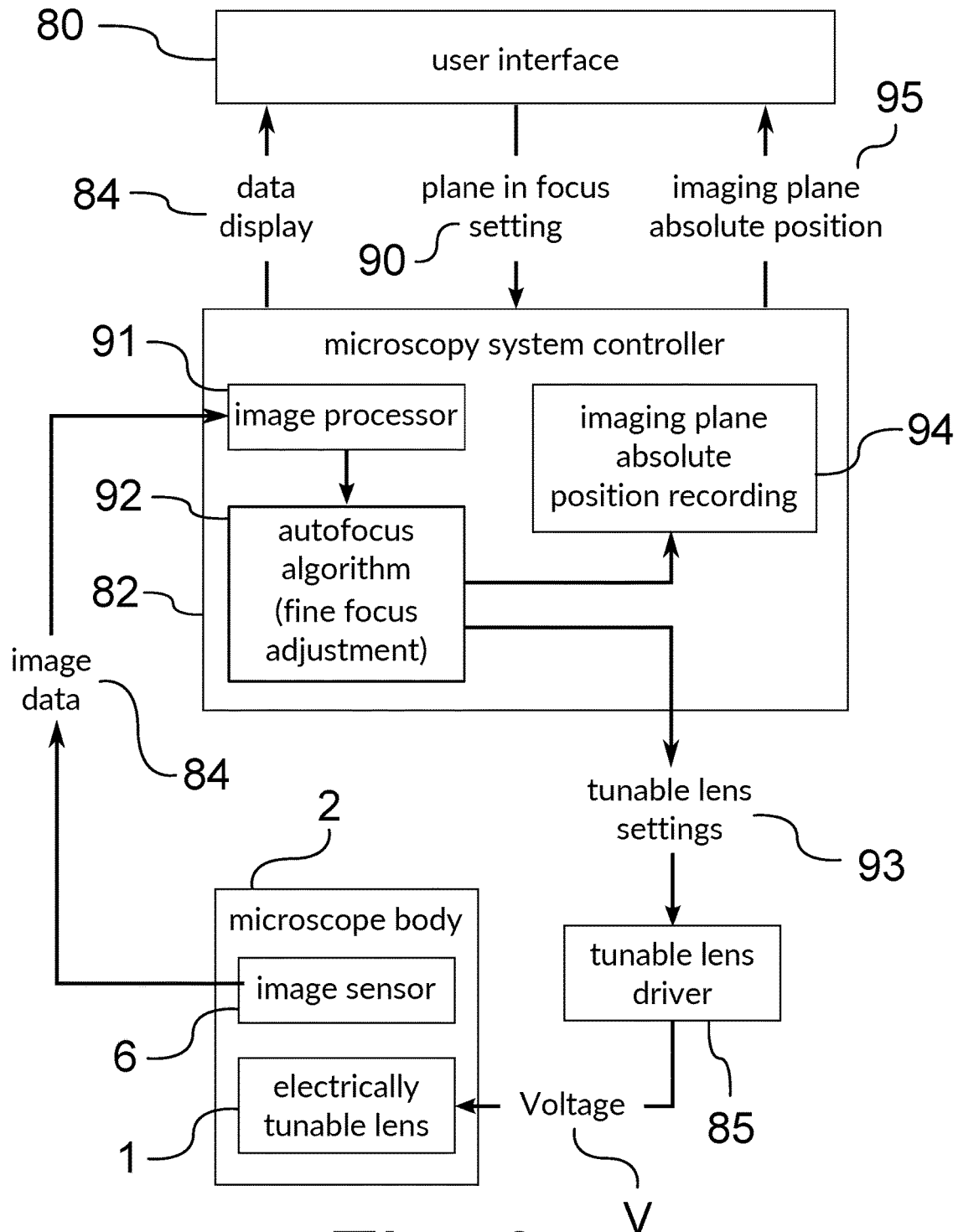
FIG. 9 is a block diagram of a microscope system with focal length adjustment for autofocus control.

Referring now to FIG. 9, an imaging system in accordance with the examples given herein and incorporating an auto-focus control is shown in a functional block diagram. The imaging system of FIG. 9 is similar to the imaging system of FIG. 7, so only differences between them will be described in detail below. Microscopy system controller 82 implements an auto-focus algorithm 92 that receives a user input 90 that defines the region of interest (region to be in focus) in the image and further receives input from an image processor 91. With the above information, auto-focus algorithm 92 generates an output tunable lens settings 93 that is provided to tunable lens driver 85 to perform auto-focusing. Generally, auto-focus algorithm 92 detects edges and other features present in the region of interest provided from the image data 84 and makes adjustments to sharpen the features in the images being produced by commanding tunable lens driver 85 with tunable lens settings 93 to change voltage V. Alternatively auto-focus can be achieved with the optimization of the return fluorescence image signal. When a fluorescent structure is in focus, the fluorescence signal is greater, i.e., the average and/or peak pixel values in the image sensor output will be stronger, and a maximizing algorithm can be used to determine the output of autofocus algorithm 92. Auto-focus can also be implemented in conjunction with image depth adjustments by setting constraints on the amount of voltage variation permitted for focusing in response to the autofocus detection. Monitoring of the object plane position in real time may be performed by an imaging plane absolute position recording subsystem 94 coupled to the microscopy system controller to provide feedback 95 to the user or a program, of the absolute image position being measured by microscopy system controller 82. In particular, when tracking biological structures in real time, for some applications the object plane moves along the optical axis and becomes out of focus (e.g., in neuroscience studies when the brain moves inside of the skull of the subject on which the cannula is attached). In other applications, users are interested in following the movements of cells over time, as the movement progresses in three dimensions, the imaging plane must be adjusted in real time (e.g., in biological cell tracking applications). Since microscopy system controller 82 provides imaging plane absolute position 95 in real time, the 3D position, the speed and the acceleration of the imaged structures may be calculated from their measured depth (i.e., the imaging plane position), along with their position in the image.

Figure 10A:
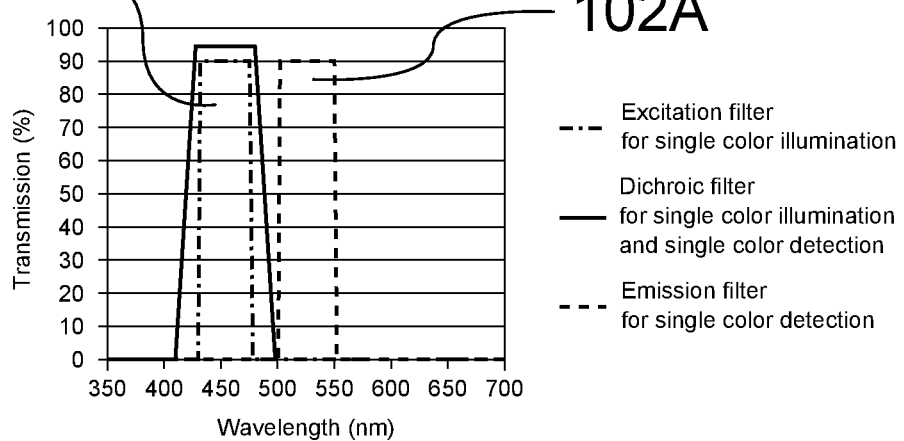
FIGS. 10A-10B are graphs depicting optical transmission band characteristics of filters that may be used within the miniaturized microscope systems depicted herein.
Figure 10B:
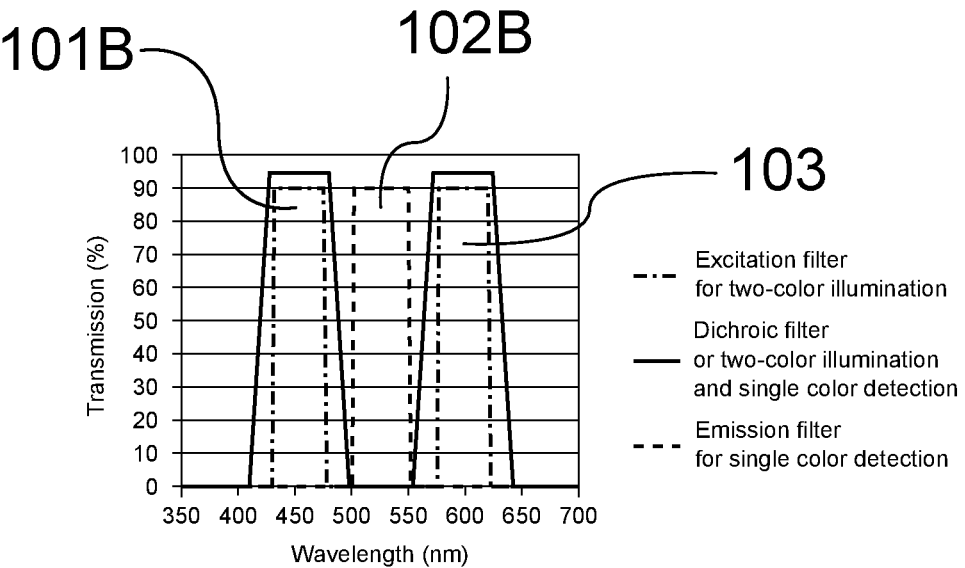

Referring now to FIG. 10A and FIG. 10B, optical bandpass characteristics of filter components that may be used in the above-described microscope systems are shown. FIG. 10A shows the passbands of filters suitable for single color fluorescence imaging, such as may be used to implement emission filter 41A and excitation filter 16A of FIG. 1. Excitation filter 16A includes one transmission band 101A for one illumination band/wavelength, which in the example corresponds to the wavelength for fluorescent excitation. Another transmission band for implementing emission filter 41A is an emission band/wavelength 102A that corresponds to the emission spectrum of the fluorescent sample. A short pass characteristic can be used for dichroic filter 11A for the through (excitation) direction and the return emissions will be reflected along detection optical path 5. FIG. 10B illustrates passbands of filters suitable for two-color illumination and single color imaging, such as may be used to implement emission filter 41A and excitation filter 16A of FIG. 1.

Excitation filter 16A in the example of FIG. 10B includes transmission bands 101B and 103 for two illumination bands/wavelengths, which in the example correspond to the wavelength for fluorescent excitation and optogenetic stimulation, respectively. Another transmission band for an emission band/wavelength 102B corresponds to the emission spectrum of the fluorescent sample, and illustrates a suitable band-pass characteristic for emission filter 41A as described above. Further, if the fluorescence emission band/wavelength transmission band 102B lies between the two illumination bands/wavelengths 101B, 103, then the band-pass characteristic of dichroic filter 11A in the through direction can be similar (or identical) to the dual transmission band characteristic of excitation filters 16A. Otherwise if the emission band/wavelength 102B is of longer wavelength(s) than the two illumination bands/wavelengths 101B, 103, then a short-pass characteristic can be used for dichroic filter 11A in the through direction.

Figure 11A:
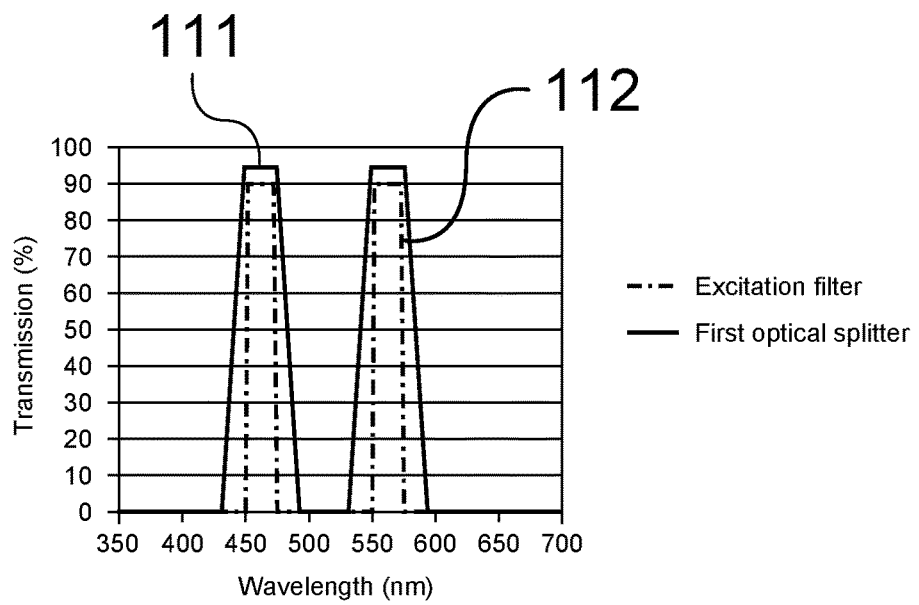
FIGS. 11A-11B are graphs depicting optical transmission band characteristics of beam splitters that may be used within the miniaturized microscope systems depicted herein.
Figure 11B:
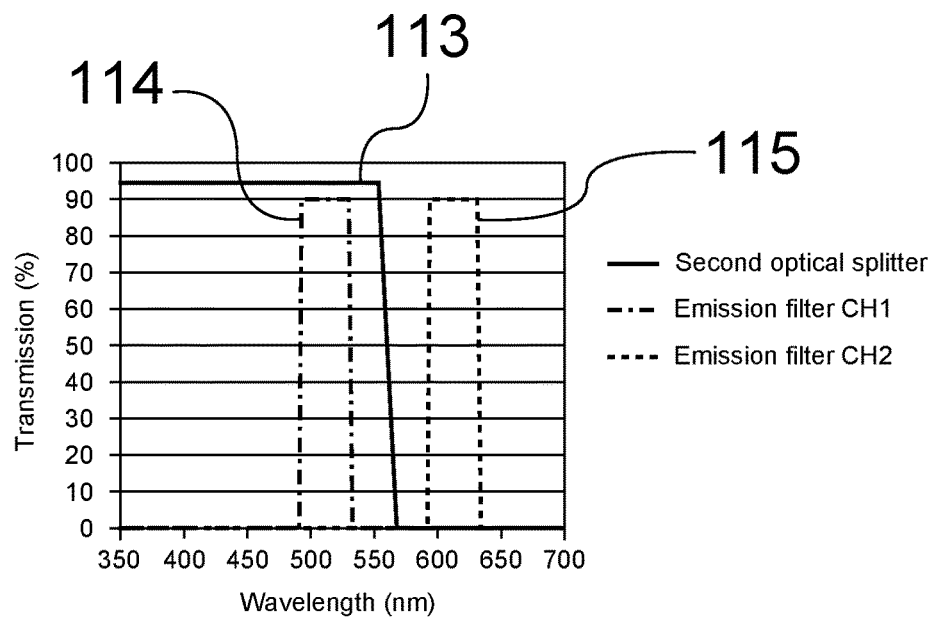

Referring now to FIG. 11A and FIG. 11B, optical characteristics of a first optical splitter (e.g., dichroic filter 11C of FIG. 7) and an excitation filter (e.g., excitation filter 16C of FIG. 7) are shown for two-illumination-color configurations. In the instant configuration, dichroic filter 11C is a dual pass-band dichroic filter that passes the two illumination wavelengths and reflects both emission wavelengths. Passbands 111 (solid lines) illustrate the passbands of dichroic filter 11C. Excitation filter 16C may generally have a narrower passband characteristic (dashed lines) 112 for purifying the spectra of the excitation illumination sources. In instances in which the two emission spectra are stimulated by a single illumination wavelength, a single passband will be present in each of dichroic filter optical splitter 11C and excitation filter 16C. Characteristics of a second optical splitter (e.g., optical splitter 43 of FIG. 7) and emission filters (e.g., emission filters 41B-41C of FIG. 7) for a two-emission-color configuration are illustrated in FIG. 11B. In the instant configuration, dichroic filter 43 has a short-pass characteristic 113 for passing a first emission wavelength and reflecting a longer second emission wavelength, thereby separating the light returning from the object plane (e.g., object planes 13A,13B) at two different corresponding wavelengths. Passbands 114 and 115 illustrate the passbands of emission filters 41B and 41C of FIG. 6, respectively.

Figure 12A:
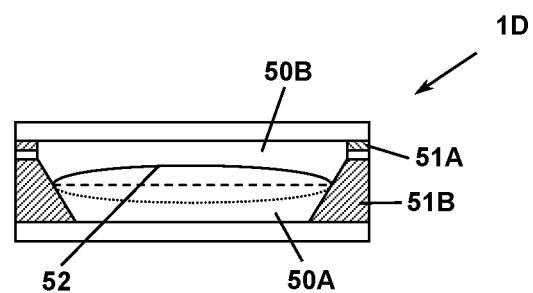
FIGS. 12A-12C are examples of electrically-tunable lenses that may be used within the miniaturized microscope systems depicted herein.
Figure 12B:
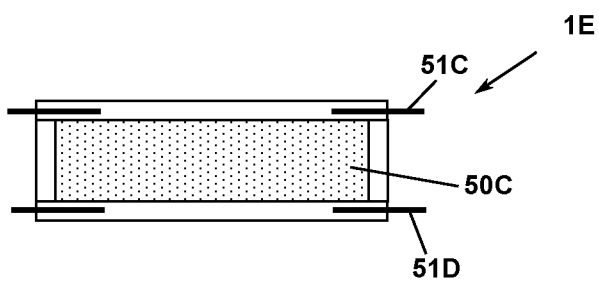
Figure 12C:
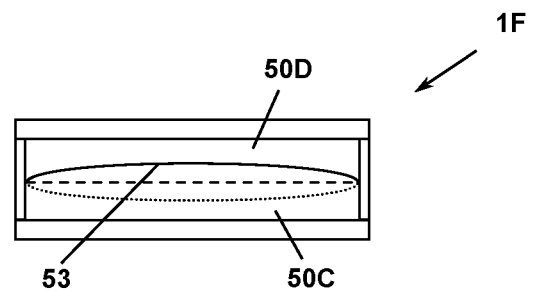

Referring now to FIGS. 12A-12C, examples of electrically-tunable lenses suitable for use in the above-described microscope systems are shown. FIG. 12A shows an electrically-tunable lens 1D, including a liquid oil media volume 50A and a water volume 50B are separated due to their non-polar and polar properties, respectively. Variation of an electric field between electrodes 51A and 51B, by varying a voltage applied therebetween, causes a boundary 52 between liquid oil media volume 50A and water volume 50B to distort, changing the curvature and thickness profile of both liquid oil media volume 50A and water volume 50B, adjusting the focal length of electrically-tunable lens 1D. FIG. 12B shows a liquid crystal electrically-tunable lens 1E, in which an applied electric field between electrodes 51C, 51D causes rotation of dipoles within a liquid-crystal media 50C and alters in a gradient profile, the effective refractive index of liquid-crystal media 50C, adjusting the focal length of electrically-tunable lens 1E. FIG. 12C shows an electrically-tunable lens 1F, including two liquid media volumes 50C and 50D of different refractive indices that are separated by a thin elastic membrane 53. By electro-mechanically altering a pressure differential between liquid media volume 50C and liquid media volume 50D, the curvature of elastic membrane 53 is altered, resulting in a change in focal length of electrically-tunable lens 1F.

While the invention has been particularly shown and described with reference to the preferred embodiment thereof, it will be understood by those skilled in the art that the foregoing and other changes in form, and details may be made therein without departing from the spirit and scope of the invention.

What is claimed:

1. A miniature microscope for imaging a region within a sample having an attached optical cannula, the microscope comprising:
   a microscope body having a first connector for receiving an optical illumination connection coupling light from at least two illumination sources;
   an optical filter having a dual band-pass characteristic for filtering the light coupled from the at least two illumination sources, wherein a first transmission band of the optical filter passes light having a first wavelength corresponding to a first one of the illumination sources and a second transmission band of the optical filter passes light having a differing second wavelength corresponding to a second one of the illumination sources, wherein the first wavelength of the first illumination source is a wavelength for optogenetic stimulation of the sample, and wherein the second wavelength of the second illumination source is a wavelength for fluorescence imaging of the sample;
   a second connector of the microscope body adapted to mechanically connect to the cannula and optically align the cannula with the microscope body and having at least one optical interface for coupling light returning from the sample to the microscope and illumination from the at least two illumination sources to the sample;
   an image sensor for generating an image from the light returning from the sample;
   a beamsplitter positioned between an objective lens and the image sensor for separating the light returning from the sample from the illumination;
   a lens system for focusing the illumination provided from the at least two illumination sources at or near a back focal plane of the objective lens, whereby the illumination provided from the at least two illumination sources to the sample is collimated at the sample, and wherein the objective lens focuses the light returning from the sample at the image sensor; and
   an electrically-tunable lens positioned between the sample and the image sensor for adjusting an optical path length between the at least one optical interface and the image sensor, whereby a focus of the image or a depth of the image within the sample is adjusted by controlling a voltage provided to the electrically-tunable lens.

2. The microscope of claim 1, further comprising the objective lens providing or coupled to the at least one optical interface of the second connector.

3. The microscope of claim 1, further comprising an optical window for sealing the second connector, wherein the microscope is configured for connection to a cannula having an integrated objective lens.

4. The microscope of claim 1, wherein the electrically-tunable lens is tuned by changing the curvature of one or both faces or an internal face of the electrically-tunable lens.

5. The microscope of claim 4, wherein the electrically-tunable lens is one of a shape-changing polymer lens, an electro-wetted lens or an electro-mechanically tunable lens.

6. The microscope of claim 1, wherein the electrically-tunable lens is tuned by changing a gradient profile of the effective refractive index of the electrically-tunable lens.

7. The microscope of claim 6, wherein the electrically-tunable lens is one of a liquid crystal lens.

8. A miniature microscope system for imaging a region within a sample, the miniature microscope system comprising:
an optical cannula configured for attachment to the sample;
a microscope having a body with a first connector for receiving at least one optical illumination connection coupling light from at least two illumination sources, a second connector adapted to mechanically connect to the cannula and optically align the cannula with the microscope body and having at least one optical interface for coupling light returning from the sample to the microscope and illumination from the at least illumination sources to the sample;
an optical filter having a dual band-pass characteristic for filtering the light coupled from the at least two illumination sources, wherein a first transmission band of the optical filter passes light having a first wavelength corresponding to a first one of the illumination sources and a second transmission band of the optical filter passes light having a differing second wavelength corresponding to a second one of the illumination sources, wherein the first wavelength of the first illumination source is a wavelength for optogenetic stimulation of the sample, and wherein the second wavelength of the second illumination source is a wavelength for fluorescence imaging of the sample;
an image sensor within the microscope body for generating an image from the light returning from the sample;
an electrically-tunable lens within the microscope body and positioned between the sample and the image sensor for adjusting an optical path length between the at least one optical interface and the image sensor, whereby a focus of the image or a depth of the image within the sample is adjusted by controlling a voltage provided to the electrically-tunable lens;
an objective lens mounted within the microscope body or the cannula and positioned between the sample and the electrically-tunable lens;
a beamsplitter within the microscope body and positioned between the objective lens and the image sensor for separating the light returning from the sample from the illumination;
a lens system within the microscope body for focusing the illumination provided from the at least one illumination source at or near a back focal plane of the objective lens, whereby the illumination provided from the at least one illumination source to the sample is collimated at the sample and wherein the objective lens focuses the light returning from the sample at the image sensor; and
a control unit for supplying a voltage to the electrically-tunable lens to control a focal length of the microscope.

9. The miniature microscope system of claim 8, wherein the control unit is coupled to the image sensor to detect a quality of focus of the microscope and implements an auto-focus controller that varies the voltage supplied to the electrically-tunable lens in conformity with the detected quality of the focus.

10. The miniature microscope system of claim 8, wherein the control unit receives an input directing a depth of the image and sets the voltage supplied to the electrically-tunable lens in conformity with the directed depth of the image.

11. A method of performing optogenetic image measurements of a biological sample, the method comprising:
mounting an optical cannula to the biological sample by attaching a stabilizer portion of the optical cannula to a surface of the biological sample;
receiving an optical illumination connection coupling light from at least one illumination source at a first connector of a microscope;
mechanically connecting to the cannula with a second connector of the microscope having at least one optical interface for coupling light returning from the sample to the microscope and illumination from the at least one illumination source to the sample;
focusing the illumination provided from the at least one illumination source at or near a back focal plane of an objective lens, whereby the illumination provided from the at least one illumination source to the sample is collimated at the sample;
focusing the light returning from the sample on an image sensor of the microscope with the objective lens at a variable focus of the image or a depth of the image within the sample is by controlling a voltage provided to an electrically-tunable lens positioned between the sample and the image sensor;
separating the light coupled from the at least one illumination source from light returning from the sample and coupled from the cannula to the second connector of the microscope with a filter; and
detecting an image of the light returning from the sample with the image sensor.

12. The method of claim 11, receiving the light returning from the sample with an objective lens integrated within the microscope.

13. The method of claim 11, wherein the mounting the optical cannula further comprises inserting an optical probe of the optical cannula into the biological sample, whereby a distal end of the optical probe receives the light returning from the object, and wherein the light returning from the sample is coupled through the optical probe to a proximal end of the optical probe to provide the optical image of the object at the second connector of the microscope.

14. The method of claim 11, further comprising:
detecting a quality of focus of the microscope; and
varying a voltage supplied to the electrically-tunable lens in conformity with the detected quality of the focus.

15. The method of claim 11, further comprising:
receiving an input directing a depth of the image; and
setting a voltage supplied to the electrically-tunable lens in conformity with the directed depth of the image.

16. The method of claim 11, wherein the receiving an optical illumination connection couples light from at least two illumination sources, and further comprising filtering the light coupled from the at least two illumination sources with an optical filter having a dual band-pass characteristic, wherein a first transmission band of the optical filter passes light having a first wavelength corresponding to a first one of the illumination sources and the second transmission band of the optical filter passes light having a differing second wavelength corresponding to a second one of the illumination sources.

17. The method of claim 16, wherein the image sensor is a first image sensor, and wherein the method further comprises:

separating the light returning from the sample and separated by the filter into a first image and a second image with a second filter integrated within the microscope;
providing the separated first image to the first image sensor; and
providing the second image to a second image sensor integrated within the microscope.

\* \* \* \* \*